(12) United States Patent
Rivest et al.

(10) Patent No.: US 11,491,053 B2
(45) Date of Patent: Nov. 8, 2022

(54) FLEXIBLE ABSORBENT BANDAGE

(71) Applicant: BIODAPTIVE ADVANCED MATERIALS, LLC, Ronkonkoma, NY (US)

(72) Inventors: Daniel Rivest, Charlotte, VT (US); Brendon Shingwoo Wai, Sydney (AU)

(73) Assignee: BIODAPTIVE ADVANCED MATERIALS, LLC, Ronkonkoma, NY (US)

( * ) Notice: Subject to any disclaimer, the term of this patent is extended or adjusted under 35 U.S.C. 154(b) by 31 days.

(21) Appl. No.: 16/832,781

(22) Filed: Mar. 27, 2020

(65) Prior Publication Data

US 2020/0306093 A1 Oct. 1, 2020

Related U.S. Application Data

(60) Provisional application No. 62/825,253, filed on Mar. 28, 2019, provisional application No. 62/832,592, filed on Apr. 11, 2019.

(51) Int. Cl.
*A61F 13/00* (2006.01)
*A61F 13/02* (2006.01)

(52) U.S. Cl.
CPC ........ *A61F 13/0213* (2013.01); *A61F 13/00* (2013.01); *A61F 13/02* (2013.01); *A61F 13/0209* (2013.01); *A61F 13/0253* (2013.01); *A61F 2013/00361* (2013.01); *A61F 2013/00604* (2013.01); *A61F 2013/00655* (2013.01); *A61F 2013/00663* (2013.01)

(58) Field of Classification Search
CPC ...... A61F 13/0213; A61F 13/02; A61F 13/00; A61F 13/0253; A61F 13/0209; A61F 2013/00663; A61F 2013/00604; A61F 2013/00361; A61F 2013/00655
See application file for complete search history.

(56) References Cited

U.S. PATENT DOCUMENTS

| | | | |
|---|---|---|---|
| 2003/0153860 A1* | 8/2003 | Nielsen | A61F 13/0253 602/43 |
| 2010/0179463 A1 | 7/2010 | Greener et al. | |
| 2010/0260824 A1* | 10/2010 | Shah | A61P 17/02 424/447 |
| 2011/0213287 A1 | 9/2011 | Lattimore et al. | |
| 2018/0289555 A1* | 10/2018 | Gogolowski | A61F 13/00038 |

FOREIGN PATENT DOCUMENTS

WO 95/07676 A1 11/2018

OTHER PUBLICATIONS

International Search Report and Written Opinion dated Jun. 12, 2020 issued in corresponding PCT International Application No. PCT/US20/025390.
International Preliminary Report on Patentability dated Sep. 28, 2021 from PCT International Patent Application PCT/US2020/025390.

* cited by examiner

*Primary Examiner* — Jacqueline F Stephens
(74) *Attorney, Agent, or Firm* — Amster, Rothstein & Ebenstein LLP

(57) ABSTRACT

A bandage includes a top film, an absorbent layer and a perforated adhesive lower layer positioned under the absorbent layer for adhering the bandage to a user's skin. The absorbent layer includes at least one incision that improves the flexibility of the bandage.

21 Claims, 5 Drawing Sheets

FLEXIBLE ABSORBENT BANDAGE

The present application claims benefit of and priority to U.S. Provisional Patent Application Ser. No. 62/825,253 filed Mar. 28, 2019, entitled FLEXIBLE ABSORBENT BANDAGE and U.S. Provisional Patent Application Ser. No. 62/832,592 filed Apr. 11, 2019 entitled FLEXIBLE ABSORBENT BANDAGE, the entire content of each of which is incorporated by reference herein.

BACKGROUND

Field of the Disclosure

The present invention relates to an absorbent bandage which may be used in a variety of applications. In particular, the present invention is directed to a bandage including an absorbent layer including at least one incision in the shape of a spiral to improve flexibility of the bandage as a whole.

Related Art

Conventional bandages typically include an absorbent layer, sometimes referred to as an absorbent core, that absorbs liquid as a wound or abrasion heals. The absorbent core, in many cases, is made of materials that are generally stiff which limits flexibility of the bandage. This may result in discomfort for the patient. In addition, since the bandage is stiff, in many cases, it is difficult for the bandage to conform properly to the part of the user's body that it is being applied to. For example, a stiff bandage may not drape properly over certain body parts such as heels and elbows, which may result in an unsecure fit. Since absorbency is important to encourage healing, effective absorbent materials must be used even if they are uncomfortable.

Accordingly, it would be beneficial to provide a bandage that avoids these and other problems.

SUMMARY

It is an object of the present disclosure to provide a bandage that is absorbent, stable and includes at least one incision in the shape of a spiral in an absorbent layer thereof to improve flexibility and comfort of the bandage.

A bandage in accordance with an embodiment of the present disclosure includes a top film; an absorbent layer having a top surface thereof adjacent to a bottom surface of the top film, the absorbent layer including at least one incision extending at least partially through the absorbent layer; and a lower layer connected to a lower surface of the absorbent layer, the lower layer including at least one opening formed therein and extending from a bottom surface thereof to a top surface thereof and including an adhesive material on the bottom surface thereof.

In embodiments, the at least one incision extends completely through the absorbent layer.

In embodiments, the at least one incision extends in a spiral shape.

In embodiments, the at least one incision includes a plurality of segments, the segments forming a plurality of concentric circles.

In embodiments, the plurality of segments are spaced apart from adjacent segments by substantially ten degrees.

In embodiments, the absorbent layer includes a hydrogel.

In embodiments, the absorbent layer includes a hydrocolloid.

In embodiments, the absorbent layer includes hydrophilic polyurethane foam.

In embodiments, the absorbent layer comprises a super absorbent polymer.

In embodiments, the absorbent layer includes: a first layer of a first material; and a second layer of a second material.

In embodiments, at least one of the first material and the second material comprises hydrophilic foam.

In embodiments, the first material comprises a super absorbent polymer and the second material comprises hydrophilic polyurethane foam.

In embodiments, the incision passes through one of the first layer and the second layer and does not pass through the other of the first layer and the second layer.

In embodiments, the incision passes through one of the first layer and the second layer and passes partially through the other of the first layer and the second layer.

In embodiments, the incision passes partially through one of the first layer and the second layer and does not pass through any portion of the other of the first layer and the second layer.

In embodiments, the bandage includes an adhesive layer provided between the top film and the adhesive layer and securing the top film to the adhesive layer.

In embodiments, the adhesive layer comprises a layer of adhesive applied to the bottom surface of the top film.

In embodiments, the adhesive layer comprises a layer of acrylic adhesive adhered to a lower surface of the top film.

In embodiments, the adhesive layer comprises a substrate with a layer of adhesive provided on a top surface and bottom surface thereof.

In embodiments, the lower layer includes a silicone based adhesive on a bottom surface thereof.

In embodiments, a method of making a bandage including: (a) providing a top film; (b) providing an absorbent layer below the top film; (c) providing at least one incision in the absorbent layer; and (d) providing a perforated lower layer below the absorbent layer lower.

BRIEF DESCRIPTION OF THE DRAWINGS

The above and related objects, features and advantages of the present disclosure will be more fully understood by reference to the following, detailed description of the preferred, albeit illustrative, embodiments of the present invention when taken in conjunction with the accompanying figures, wherein.

DETAILED DESCRIPTION OF THE EXEMPLARY EMBODIMENTS

Figure 1:
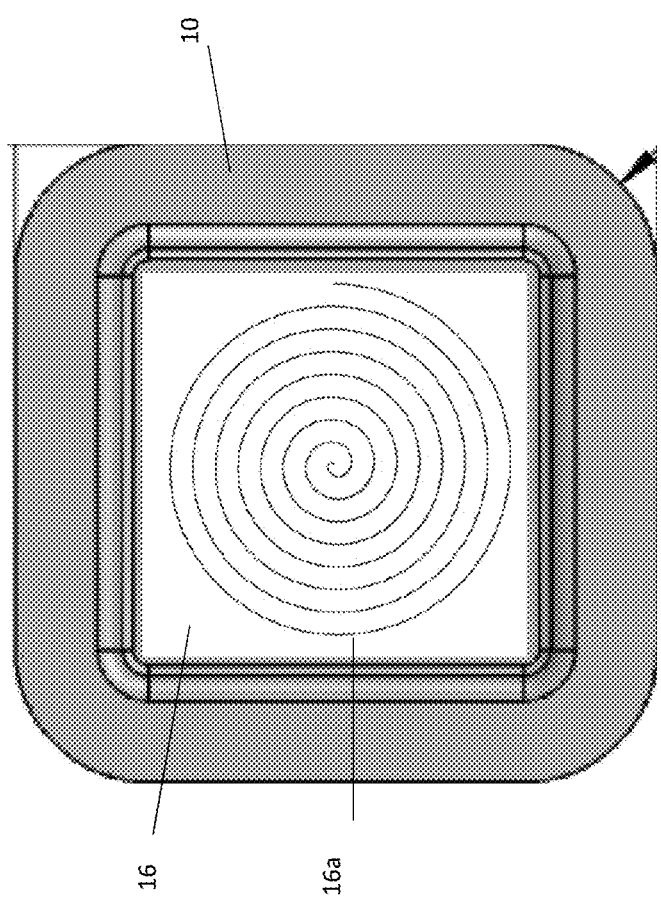
FIG. 1 illustrates an exemplary embodiment of a bandage including an incision in the absorbent layer in accordance with an embodiment of the present disclosure.
Figure 2:
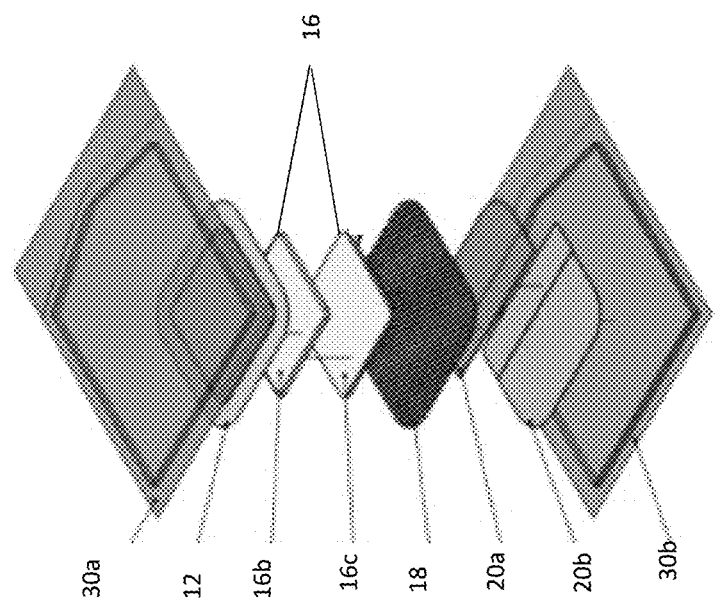
FIG. 2 illustrates an exploded view of a bandage in accordance with an exemplary embodiment of the present disclosure.
Figure 3:
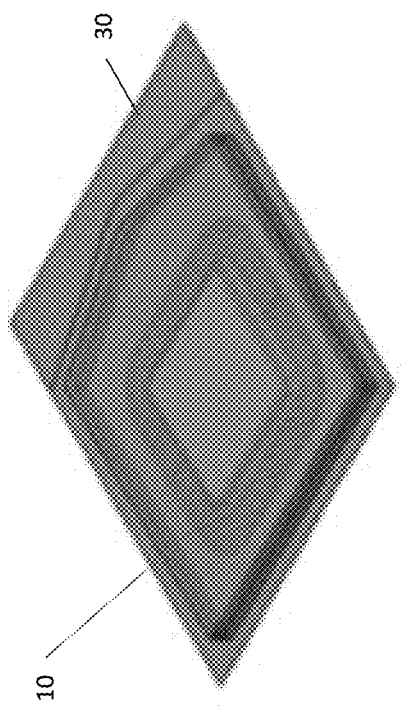
FIG. 3 illustrates the bandage of FIG. 1 in a packaging element before use.

A bandage 10 in accordance with an embodiment of the present disclosure is illustrated in FIG. 1. In embodiments, the bandage 10 may include an absorbent core 16 positioned substantially in a center of the bandage. In embodiments, a top film 12 may be provided above the absorbent core 16 (see FIG. 2, for example). In FIG. 1, the term "above" refers to a position further from a user's skin when the bandage 10 is applied thereto. In embodiments, this top film 12 may be made of polyurethane, however, the film 12 is not limited to this material and may be made of any suitable material.

In embodiments, an adhesive layer (not shown) may be provided under the top film layer 12, closer to the patient's skin when the bandage 10 is in place. In embodiments, the adhesive layer keeps the top film layer 12 in place and prevents buckling of the bandage 10. In embodiments, the adhesive layer may be implemented as a continuous or discontinuous coating of adhesive provided on a bottom (lower) surface of the film 12, rather than as a separate layer of material. In embodiments, the adhesive layer may be made of or include acrylic adhesive, but any suitable adhesive may be used. In embodiments, the adhesive layer may be a separate layer including a substrate with an adhesive material provided on a top (upper) and bottom (lower) surface thereof. In embodiments, the adhesive may be applied in a pattern using a roller and template. In embodiments, different patterns may be used for the adhesive.

In embodiments, the adhesive layer may be used to connect the film layer 12 to the absorbent layer or core 16. An advantage of using this configuration is that the adhesive layer prevents bunching or folding of the bandage 10 during application and use. In embodiments, the adhesive layer may not be used at all.

In embodiments, the absorbent layer or core 16 may be provided under the adhesive layer and in contact therewith such that it is adhered to the top film 12. In embodiments, the absorbent layer or core 16 may be directly in contact with the film 12. In embodiments, the absorbent layer or core 16 may be made of a hydrogel or a hydrocolloid and absorbs moisture from the wound covered by the bandage 10. While a hydrocolloid or a hydrogel are preferred materials to be included on the layer 16, other suitably absorbent materials may be used, provided that they are sufficiently absorbent. In embodiments, the absorbent layer or core 16 may be translucent or transparent. In embodiments, the absorbent core 16 may include multiple layers. In embodiments, the absorbent core 16 may include at least one layer of hydrophilic foam. In embodiments, silicone in combination with superabsorbent polymers or fibers may be used to form the absorbent layer or core 16, or a portion thereof. In embodiments, the absorbent layer or core 16 may include polyvinyl alcohol foam. In embodiments, the absorbent layer or core 16 may be made of a super absorbent polymer. In embodiments, such as that illustrated in FIG. 2, the absorbent layer 16 may include two layers of material. In embodiments, a top layer 16b of the core 16 may be made of a super absorbent polymer while the bottom layer 16c of the core 16 may be made of hydrophilic polyurethane foam. In embodiments, adhesive may be provided to connect the two layers 16b, 16c together. In embodiments, an adhesive layer, with adhesive on both sides may be provided to connect the layers 16b, 16c. In embodiments, no adhesive may be used between layers of the absorbent layer 16. In embodiments, the absorbent layer or core 16 may include additional layers. In embodiments, the absorbent layer or core 16 may include a single layer. In embodiments, the absorbent layer or core 16 may be made of, or include, other materials provided that it is sufficiently absorbent to absorb substantial fluid from the wound without requiring replacement, since frequent removal of the bandage 10 increases the risk of infection. In embodiments, the absorbent layer 16 may be sufficiently absorbent to absorb fluid from a wound continuously.

Since wounds excrete fluid at different rates depending on the condition of the wound, bandages may need to be changed more frequently depending on the rate of healing of the wound. In embodiments, a caregiver may monitor the status of the bandage 10 and will change it after it has absorbed sufficient fluid such that it swells to the point that it is uncomfortable to the patient. In embodiments, the patient them self may monitor the status of the bandage 10 and determine when it becomes uncomfortable. In embodiments, the bandage 10 may be removed where observation indicates that a wound is not healing or where a wound is developing for treatment and a new bandage may be applied. In embodiments, the absorbent layer or core 16 may include one or more active ingredients. In embodiments, the active ingredient may be an antimicrobial substance. In embodiments, the active ingredient may be an additive that provides an indication of infection in the wound. In embodiments, an additive may be provided to reduce odors. In embodiment, other active ingredients may be added to provide other features.

In embodiments, a perforated adhesive lower layer 18 may be provided under the absorbent layer 16 between the absorbent material and the user's skin. In embodiments, the perforated adhesive lower layer 18 may be implemented using a polyurethane, or other film with a silicone based adhesive provided thereon to secure the bandage 10 to the user's skin. In embodiments, an acrylic based adhesive may be provided on the upper surface of the perforated adhesive layer 18 to secure it to the absorbent layer 16 while a silicone based adhesive is provided on a bottom surface and contacts the user's skin. In embodiments, the silicone adhesive on the lower surface of the perforated adhesive lower layer 18 adheres to the user's skin around the wound while avoiding a strong bond with the wound. In embodiments, other materials may be used to make the layer 18, provided that the adhesive that faces the user's skin is silicone based. In embodiments, perforations in the adhesive lower layer 18 allow fluid to pass from the wound on the user's skin, through the lower layer 18 and into the absorbent layer 16 where it is absorbed. In embodiments, the perforated adhesive lower layer 18 provides a stable and firm connection to the user's skin to keep the bandage 10 in place while being relatively comfortable. In addition, the silicone based adhesive allows for relatively easy removal, without damaging the wound.

Figure 1B:
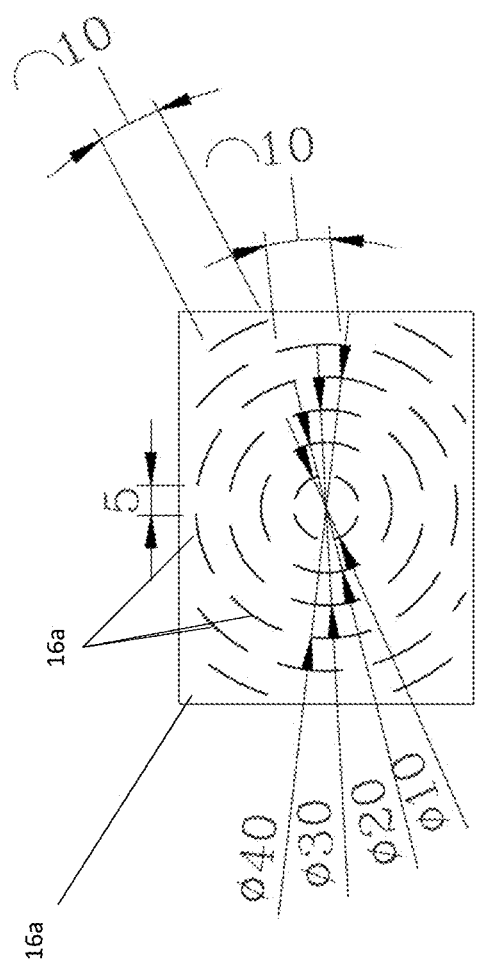
FIG. 1B illustrates an alternative shape of the incision included in FIG. 1.

In embodiments, the absorbent layer 16 includes at least one incision 16a, as can be seen in FIG. 1, for example. In embodiments, the incision 16a may be in the shape of a spiral that begins substantially at a center of the absorbent layer 16 and extends toward the edge thereof. In embodiments the incision 16a may extend through the entire absorbent layer 16. In embodiments, the spiral incision 16a may extend through only a portion of the absorbent layer. In embodiments, where the absorbent layer 16 includes multiple layers 16b, 16c, the incision may extend completely through the foam layer 16c and not through the polymer layer 16b. In embodiments, the incision 16a may extend completely through both the foam layer 16c and the polymer layer 16b. In embodiments, the incision 16a may extend completely through the foam layer 16c and partially through the polymer layer 16b or vice versa. In embodiments, the incision 16a may extend partially through the foam layer 16c, and not into the polymer layer 16b at all or vice versa. In embodiments, the incision 16a may pass through one or more layers of the core 16 and not through others. In embodiments, the incision 16a may pass through one or more layers of the core 16 and partially through others. The incision 16a allows for flexing of the absorbent layer 16 so that the bandage 10 is more flexible. As a result, the bandage 10 is generally more comfortable to wear and flexes with the user as they move such that it stays better attached to the user's body. In addition, the incision 16a allows the bandage 10 to bend and flex to conform the shape of the user's body at the point where it is attached to provide for a more secure connection to the user's skin. In embodiments, the spiral shape of the incision 16a allows for flexing in all directions from the center out to the edges of the absorbent layer or core 16. In embodiments, the incision 16a may include a series of discontinuous concentric circles, or portions thereof, as can be seen in FIG. 1B, for example. In embodiments, each of the segments of the incision 16a may be about 10 mm long, however other sizes may be used depending on size and shape of the bandage 10 and the absorbent layer 16. In embodiments, a 5 mm space may be provided between adjacent segments in the same circle, however, this distance may change depending on size and shape of the bandage 10 and the absorbent layer 16. In embodiments, each of the segments of the incision 16a may be offset from a successive segment in an adjacent circle by 10 degrees as can be seen in FIG. 1B. It is noted that these dimensions are exemplary and other dimensions may be used. These patterns for the incision 16a substantially improve flexibility and comfort of the absorbent layer 16 and the bandage 10 as a whole.

In embodiments, the bandage 10 preferably has a layered, sandwich-like structure in which the film 12 and perforated silicone adhesive lower layer 18 extend beyond the periphery of the absorbent layer or core 16 around a periphery of the bandage 10. In embodiments, all of the layers of the bandage 10 may be translucent to allow viewing of the user's skin, including a wound under the bandage 10, without removing the bandage to allow a user to monitor healing of the wound easily and without removing the bandage, thus reducing the risk of infection.

In embodiments, one or more protective liners 20a, 20b may be provided to cover the perforated silicone adhesive lower layer 18 prior to use. In embodiments, the protective liners 20a, 20b are preferably removable from the adhesive layer 18 and are preferably made of polyethylene. In embodiments, the liners 20a, 20b may be made of a coated paper material. In embodiments, the liners 20a, 20b may be made of other materials, provided that they allow them to be removable from the adhesive layer 18 without damaging the adhesive.

In embodiments, a packaging element 30 may be provided to store the bandage 10 before use. In embodiments, the packaging element 30 may be made of a combination of paper and polyethylene, or paper and forms a pouch or pocket in which the bandage 10 may be stored. In embodiments, the packaging element 30 may be made of any other suitably durable material. In embodiments, the packaging element 30 may be made of a material that is suitable to allow for sterilization of the bandage 10 while in place in the packaging element. In embodiment the packaging element 30 may be made of a material that is impervious to liquids. In embodiments, the packaging element 30 may be made of a material that allows liquid to exit, but not enter, or that allows liquid to enter but not exit. In embodiments, the packaging element 30 may be transparent or include transparent portions. In embodiments, the packaging element 30 includes an upper part 30a and a lower part 30b with the bandage 10, including the layers discussed above, sandwiched between the upper and lower parts.

In embodiments, when the absorbent layer 16 uses a hydrocolloid material, an additional layer may be provided in the absorbent layer 16 above the hydrocolloid material. In embodiments, the hydrocolloid material tends to be fairly hard, particularly as it absorbs moisture. In embodiments, the additional layer may be made of a hydrogel or silicone and provides additional cushioning or padding in the bandage 10. In embodiments, the incision 16a may pass completely or partially through the additional layer as well. In embodiments, the additional layer may be made of silicone in combination with superabsorbent polymers or fibers. In embodiments, the cushion layer may be made of or include polyvinyl alcohol foam. In embodiments, the cushion layer may be the foam layer 16c discussed above. Comfort may be a key consideration for the bandage 10 since those with serious wounds may already be uncomfortable based on their injuries.

In embodiments, as illustrated, the bandage 10 may have a square shape, however, is not limited to this shape. In embodiments, the bandage 10 may be provided in other shapes. In embodiments, the bandage 10 may be smaller or larger than illustrated such that it is suitable for use with wounds of different sizes and on different portions of a user's body. In embodiments, the bandage 10 will be available in a variety of sizes, preferable between 1 and 90 square inches.

The bandage 10 is flexible and comfortable for the patient to wear based on the inclusion of the spiral incision 16a and protects wound sites for long term use. The spiral incision 16a also improves flexibility of the bandage and allows the bandage 10 to drape properly on any part of the user's body such that it can be properly secured to the user's skin.

Figure 4:
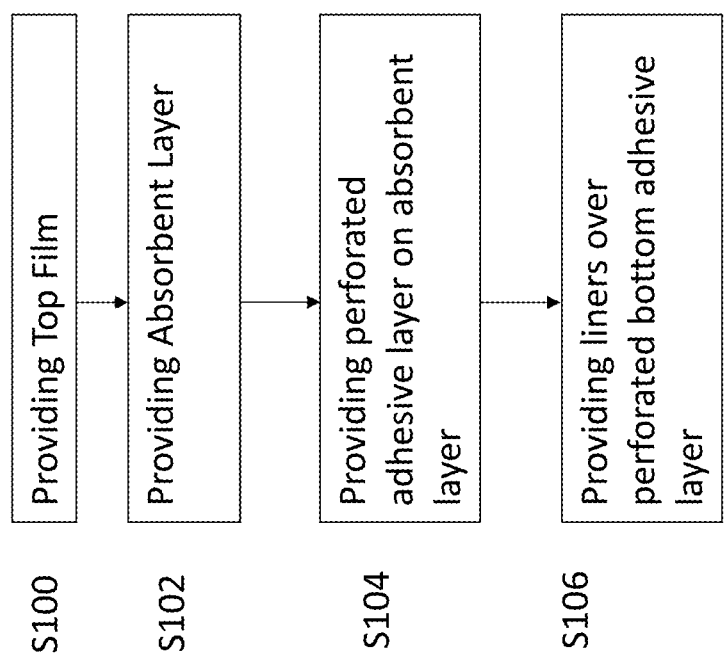
FIG. 4 is an exemplary flow chart for a method of making the bandage of FIG. 1.

In embodiments, the bandage 10 may be made by providing the top film 12 in step S100 of FIG. 4. Thereafter, the absorbent layer or core 16 may be provided below the top film 12 in step S102. In embodiments, adhesive or an adhesive layer may be provided between the film 12 to the absorbent layer 16. In embodiments, the adhesive may be provided as an adhesive layer. In embodiments, the adhesive may be applied to the top film 12 and/or the absorbent layer or core 16 to connect them together. In embodiments, no adhesive may be used. In embodiments, the absorbent layer 16 may already include the incision 16a before or after it is connected to the top film 12. In embodiments, an additional step may be provided to provide the incision 16a into the absorbent layer 16. In embodiments, the incision 16a may pass all the way through the absorbent layer 16 or partially through the absorbent layer. At a step S104, the perforated adhesive lower layer 18 is provide on bottom of the absorbent layer 16. In embodiments, the perforated adhesive lower layer 18 includes a silicone based adhesive on a bottom surface thereof that faces the user's skin when the bandage 10 is in use. In embodiments, the liners 20a, 20b may be used to cover the perforated adhesive lower layer in step S106. In embodiments, the bandage 10 may be placed into the packaging element 30. In embodiments, the bandage 10 may not be individually packaged in the packaging element 30.

Although the present invention has been described in relation to particular embodiments thereof, many other variations and modifications and other uses will become apparent to those skilled in the art. It is preferred, therefore, that the present invention be limited not by the specific disclosure herein.

What is claimed is:

1. A bandage comprising:
   a top film;

an absorbent layer having a top surface thereof adjacent to a bottom surface of the top film, the absorbent layer including at least one incision extending at least partially through the absorbent layer;

an adhesive layer provided between the top film and the absorbent layer and securing the top film to the absorbent layer; and a lower layer connected to a lower surface of the absorbent layer, the lower layer including at least one opening formed therein and extending from a bottom surface thereof to a top surface thereof and including an adhesive material on the bottom surface thereof.

2. The bandage of claim 1, wherein the at least one incision extends completely through the absorbent layer.

3. The bandage of claim 1, wherein the at least one incision extends in a spiral shape.

4. The bandage of claim 1, wherein the at least one incision comprises a plurality of segments, the segments forming a plurality of concentric circles.

5. The bandage of claim 4, wherein the plurality of segments are spaced apart from adjacent segments by substantially ten degrees.

6. The bandage of claim 1, wherein the absorbent layer comprises a hydrogel.

7. The bandage of claim 1, wherein the absorbent layer comprises a hydrocolloid.

8. The bandage of claim 1, wherein the absorbent layer comprises hydrophilic polyurethane foam.

9. The bandage of claim 1, wherein the absorbent layer comprises a super absorbent polymer.

10. The bandage of claim 1, wherein the absorbent layer comprises:
a first layer of a first material;
a second layer of a second material.

11. The bandage of claim 10, wherein at least one of the first material and the second material comprises hydrophilic foam.

12. The bandage of claim 10, wherein the first material comprises a super absorbent polymer and the second material comprises hydrophilic polyurethane foam.

13. The bandage of claim 10, wherein the incision passes through one of the first layer and the second layer and does not pass through the other of the first layer and the second layer.

14. The bandage of claim 10, wherein the incision passes through one of the first layer and the second layer and passes partially through the other of the first layer and the second layer.

15. The bandage of claim 10, wherein the incision passes partially through one of the first layer and the second layer and does not pass through any portion of the other of the first layer and the second layer.

16. The bandage of claim 1, wherein the adhesive layer comprises a layer of adhesive applied to the bottom surface of the top film.

17. The bandage of claim 1, wherein the adhesive layer comprises a layer of acrylic adhesive adhered to a lower surface of the top film.

18. The bandage of claim 1, wherein the adhesive layer comprises a substrate with a layer of adhesive provided on a top surface and bottom surface thereof.

19. The bandage of claim 1, wherein the lower layer comprises a silicone based adhesive on the bottom surface thereof.

20. A method of treating a wound comprising:
(a) providing a top film;
(b) providing an absorbent layer below the top film;
(c) providing at least one incision in the absorbent layer;
(d) providing a perforated lower layer below the absorbent layer; and
(e) providing an adhesive layer between the top film and the absorbent layer securing the top film to the absorbent layer.

21. A bandage comprising:
a top film;
an absorbent layer having a top surface thereof adjacent to a bottom surface of the top film, the absorbent layer including a continuous spiral shaped incision extending at least partially through the absorbent layer; and
a lower layer connected to a lower surface of the absorbent layer, the lower layer including at least one opening formed therein and extending from a bottom surface thereof to a top surface thereof and including an adhesive material on the bottom surface thereof.

* * * * *